(12) United States Patent
Pandita et al.

(10) Patent No.: US 11,322,229 B2
(45) Date of Patent: May 3, 2022

(54) SYSTEM AND METHOD OF DOCUMENTING CLINICAL TRIALS

(71) Applicant: Innoplexus AG, Eschborn (DE)

(72) Inventors: Esha Pandita, Aligarh (IN); Vivek Verma, Pune (IN); Sunil Patel, Di-Patan (IN); Vatsal Agarwal, Rampur (IN)

(73) Assignee: Innoplexus AG, Eschborn (DE)

( * ) Notice: Subject to any disclaimer, the term of this patent is extended or adjusted under 35 U.S.C. 154(b) by 206 days.

(21) Appl. No.: 16/143,976

(22) Filed: Sep. 27, 2018

(65) Prior Publication Data

US 2020/0105379 A1   Apr. 2, 2020

(51) Int. Cl.
  G16H 10/20    (2018.01)
  G16H 70/00    (2018.01)
  G06N 20/00    (2019.01)
  G16H 15/00    (2018.01)
  G06F 16/2457  (2019.01)

(52) U.S. Cl.
  CPC ....... *G16H 10/20* (2018.01); *G06F 16/24575* (2019.01); *G06N 20/00* (2019.01); *G16H 15/00* (2018.01); *G16H 70/00* (2018.01)

(58) Field of Classification Search
  CPC ........ G16H 10/20; G16H 70/00; G16H 15/00; G06N 20/00
  See application file for complete search history.

(56) References Cited

U.S. PATENT DOCUMENTS

| | | | | |
|---|---|---|---|---|
| 2003/0065669 | A1* | 4/2003 | Kahn | G06Q 10/10 |
| 2004/0267566 | A1* | 12/2004 | Badgett | G16H 70/20 |
| | | | | 705/2 |
| 2008/0010254 | A1* | 1/2008 | Settimi | G06Q 10/06 |
| 2009/0313045 | A1* | 12/2009 | Boyce | G16H 10/20 |
| | | | | 705/3 |
| 2010/0088245 | A1* | 4/2010 | Harrison | G06Q 30/018 |
| | | | | 705/317 |
| 2010/0299335 | A1* | 11/2010 | Gopalakrishnan | G16H 10/60 |
| | | | | 707/756 |
| 2011/0301982 | A1* | 12/2011 | Green, Jr. | G16H 50/20 |
| | | | | 705/3 |

(Continued)

*Primary Examiner* — Michael Tomaszewski
*Assistant Examiner* — Jay M. Patel
(74) *Attorney, Agent, or Firm* — Ziegler IP Law Group, LLC (57) ABSTRACT

Disclosed is a system for documenting clinical trials, the system when operated identifies at least one publication related to a clinical trial entry to obtain documented clinical trial. The system comprises: an information repository comprising plurality of publications; a clinical trials registry database comprising a plurality of clinical trial entries; and a server arrangement. The server arrangement is configured to: obtain the plurality of publications; analyze the plurality of publications, using a filtering module, to determine a filtered set of publications; obtain the plurality of clinical trial entries; analyze a context of each of the publications in the filtered set and each of the plurality of clinical trial entries using a mapping module to identify a relationship of each of the publication with at least one of the plurality of clinical trial entries; and associate the plurality of clinical trial entries with publications related thereto to obtain documented clinical trials.

8 Claims, 2 Drawing Sheets

(56) References Cited

U.S. PATENT DOCUMENTS

| | | | | |
|---|---|---|---|---|
| 2012/0323796 | A1* | 12/2012 | Udani | G16H 20/17 |
| | | | | 705/80 |
| 2013/0332190 | A1* | 12/2013 | Hoffman | G06Q 10/10 |
| | | | | 705/3 |
| 2013/0346104 | A1* | 12/2013 | Pillai | G16H 10/60 |
| | | | | 705/3 |
| 2014/0046926 | A1* | 2/2014 | Walton | G16H 10/20 |
| | | | | 707/710 |
| 2014/0236623 | A1* | 8/2014 | Shiovitz | G16H 10/20 |
| | | | | 705/2 |
| 2014/0289001 | A1* | 9/2014 | Shelton | G06F 21/6254 |
| | | | | 705/7.29 |
| 2014/0316793 | A1* | 10/2014 | Pruit | G16H 10/20 |
| | | | | 705/2 |
| 2015/0012482 | A1* | 1/2015 | Alsanousi | G16H 50/70 |
| | | | | 707/603 |
| 2015/0161336 | A1* | 6/2015 | Kalathil | G16H 10/60 |
| | | | | 705/3 |
| 2015/0324527 | A1* | 11/2015 | Siegel | G16B 50/00 |
| | | | | 705/3 |
| 2016/0004820 | A1* | 1/2016 | Moore | G06F 21/604 |
| | | | | 705/3 |
| 2017/0061102 | A1* | 3/2017 | Weber | G06Q 50/01 |
| 2017/0199189 | A1* | 7/2017 | Wade | G16H 50/30 |
| 2018/0052928 | A1* | 2/2018 | Liu | G06F 16/2228 |
| 2019/0027232 | A1* | 1/2019 | Beim | G16B 50/00 |
| 2019/0304575 | A1* | 10/2019 | Beltre | G06N 5/022 |

* cited by examiner

SYSTEM AND METHOD OF DOCUMENTING CLINICAL TRIALS

TECHNICAL FIELD

The present disclosure relates generally to data processing; and more specifically, to processing of pharmaceutical data.

Furthermore, the present disclosure relates to systems and methods of documenting clinical trials.

BACKGROUND

With the advent of technology and knowledge in the field of medical sciences, scientists and researchers get lots of opportunity to perform clinical researches for new treatments and known interventions using a drug, a vaccine, a dietary choice, a dietary supplement, a medical device and so forth. Such clinical researches are required to be registered with one or more regulatory authorities in form of clinical trials, wherein the clinical trials are researches and observations obtained from the clinical researches carried out by the scientists and researchers. Furthermore, each of the clinical trials registered with the regulatory authorities may have publications (such as research papers, journals, review papers, conference proceedings and the like) associated with it. Moreover, publications associated (namely, linked, connected) with a specific clinical trial are used for purposes such as extending research on a new treatment and/or a known intervention in the clinical trial, using the new treatment and/or the known intervention for treatment of a patient, analyzing a use and side effects of using the new treatment and/or the known intervention. Notably, for achieving the aforementioned purposes it becomes indispensable to identify and document the associations between the clinical trial and publications.

Conventionally, such associations between the clinical trial and the publications is established by way of search strings using one or more search engines. Notably, the search strings include keywords related to the clinical trial. Consequently, the search engines provide publications having similar keywords with the clinical trial. However, the publications having similar keywords with the clinical trial may not actually have an association with the clinical trial. Therefore, such an approach for establishing associations between the clinical trial and the publications is inefficient, prone to errors, time and labour consuming and not optimized. Nowadays, the associations between the clinical trial and the publications is identified based on a weightage score provided to clinical trial parameters such as interventions, disease mentioned, age group, number of patients enrolled and so forth. Notably, in such a technique an association between the clinical trial and the publications is identified (namely, mapped) if a given parameter in the clinical trial and the publication matches and the weightage score thereof exceeds a predetermined threshold. However, such an approach is prone to error, requires human interventions (manual effort). In addition, in an instance of high threshold, such an approach may lead to unidentified associations and in an instance of low threshold it may provide irrelevant associations between the clinical trial and the publications. Alternatively, the associations between the clinical trial and the publications is identified and documented by applying a rule-based technique. Such rule-based techniques include condition-based approach for identification and documentation of associations between the clinical trial and the publications. In an example, a publication may have an association with a clinical trial if they have common author. However, an author of the clinical trial may have one or more publications on different topics or in different context. In such an instance, the rule-based techniques do not provide optimal results and prove to be inefficient in identifying and documenting associations between the clinical trial and the publications.

Therefore, in light of the foregoing discussion, there exists a need to overcome the aforementioned drawbacks associated with documentation of associations between clinical trials and publications.

SUMMARY

The present disclosure seeks to provide a system for documenting clinical trials. The present disclosure also seeks to provide a method of documenting clinical trials. The present disclosure seeks to provide a solution to the existing problem of scattered and insufficient information associated with clinical trials. An aim of the present disclosure is to provide a solution that overcomes at least partially the problems encountered in prior art, and provides an efficient, effective, robust and easy to implement approach for identifying associations between clinical trials and one or more publications related thereto.

In one aspect, an embodiment of the present disclosure provides a system for documenting clinical trials, the system when operated identifies at least one publication related to a clinical trial entry to obtain a documented clinical trial, wherein the system comprises:

an information repository comprising a plurality of publications;

a clinical trials registry database comprising a plurality of clinical trial entries; and a server arrangement communicably coupled to the information repository and the clinical trials registry database, wherein the server arrangement is configured to:

obtain the plurality of publications from the information repository;

analyze the plurality of publications, using a filtering module, to determine a filtered set of publications, wherein each of the publications in the filtered set is related to clinical trial research;

obtain the plurality of clinical trial entries from the clinical trials registry database;

analyze a context of each of the publications in the filtered set and each of the plurality of clinical trial entries using a mapping module to identify a relationship of each of the publication with at least one of the plurality of clinical trial entries; and     associate the plurality of clinical trial entries with publications related thereto to obtain documented clinical trials.

In another aspect, an embodiment of the present disclosure provides a method of documenting clinical trials, the method is operable to identify at least one publication related to a clinical trial entry to obtain a documented clinical trial, wherein the method comprises:

obtaining a plurality of publications from an information repository;

analyzing the plurality of publications, using a filtering module, to determine a filtered set of publications, wherein each of the publications in the filtered set is related to clinical trial research;

obtaining a plurality of clinical trial entries from a clinical trials registry;

analyzing a context of each of the publications in the filtered set and each of the plurality of clinical trial entries using a machine learning module to identify a relationship of each of the publication with at least one of the plurality of clinical trial entries; and associating the plurality of clinical trial entries with publications related thereto to obtain documented clinical trials.

Embodiments of the present disclosure substantially eliminate or at least partially address the aforementioned problems in the prior art, and enable easier, faster and collective retrieval of information (in form of publications) related with clinical trials.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those skilled in the art will understand that the drawings are not to scale. Wherever possible, like elements have been indicated by identical numbers.

Embodiments of the present disclosure will now be described, by way of example only, with reference to the following diagrams wherein.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

In one aspect, an embodiment of the present disclosure provides a system for documenting clinical trials, the system when operated identifies at least one publication related to a clinical trial entry to obtain a documented clinical trial, wherein the system comprises:

an information repository comprising a plurality of publications;

a clinical trials registry database comprising a plurality of clinical trial entries; and a server arrangement communicably coupled to the information repository and the clinical trials registry database, wherein the server arrangement is configured to:

obtain the plurality of publications from the information repository;

analyze the plurality of publications, using a filtering module, to determine a filtered set of publications, wherein each of the publications in the filtered set is related to clinical trial research;

obtain the plurality of clinical trial entries from the clinical trials registry database;

analyze a context of each of the publications in the filtered set and each of the plurality of clinical trial entries using a mapping module to identify a relationship of each of the publication with at least one of the plurality of clinical trial entries; and associate the plurality of clinical trial entries with publications related thereto to obtain documented clinical trials.

In another aspect, an embodiment of the present disclosure provides a method of documenting clinical trials, the method is operable to identify at least one publication related to a clinical trial entry to obtain a documented clinical trial, wherein the method comprises:

obtaining a plurality of publications from an information repository;

analyzing the plurality of publications, using a filtering module, to determine a filtered set of publications, wherein each of the publications in the filtered set is related to clinical trial research;

obtaining a plurality of clinical trial entries from a clinical trials registry;

analyzing a context of each of the publications in the filtered set and each of the plurality of clinical trial entries using a machine learning module to identify a relationship of each of the publication with at least one of the plurality of clinical trial entries; and associating the plurality of clinical trial entries with publications related thereto to obtain documented clinical trials.

The present disclosure provides a system and method of documenting clinical trials that allows for a fully-automated, faster, efficient, and optimised approach of accessing publications related to clinical trials. Furthermore, the invention disclosed herein reduces manual effort, time, processing complexity and cost of accessing publications related to clinical trials. Moreover, the system and method disclosed herein substantially eliminates a probability of accessing redundant, uncertain and inauthentic information related to the clinical trials. The system can be implemented using conventional hardware components. Furthermore, the method disclosed herein is platform independent.

Notably, the invention enables the hardware components used for implementation thereof to work in more effective and efficient manner by reducing processing complexity and time complexity required for processing data while documenting clinical trials. The system and method disclosed herein simplifies and optimizes a process of identifying, collecting, organizing and accessing information, publications related with clinical trials by employing machine learning techniques. Therefore, an optimal solution for identifying relevant and authentic publications related with the clinical trials is provided by performing contextual analysis of available publications and clinical trials.

The term "clinical trial entry" relates to a information relating to clinical research associated with a new treatment or known intervention such as a drug, a vaccine, a dietary plan, a dietary compliment, a medical device. The clinical trial relates to a medical experiment or clinical research that is either in progress or has been concluded. A clinical trial entry for a clinical trial that has concluded includes details like clinical trial ID, author of the clinical trial, the new treatment or intervention for which the clinical trial was carried out, number of patients enrolled in the clinical trial, duration of the clinical trial observations, geographical location for conduction of the clinical trial and results of the clinical trial. Furthermore, a clinical trial entry for an ongoing clinical trial comprises fewer details as compared to the clinical trial that has concluded. Notably, the clinical trial entry for the ongoing clinical trial comprises a clinical trial ID, status of the clinical trial (for example, recruitment of patients), a phase of the clinical trial and so forth. It is to be understood that details included in the clinical trial entry for the ongoing clinical trial get updated (such as added, modified, deleted) as the clinical trial progresses. The clinical trial generates information associated with safety and efficacy associated with use of the new treatment or intervention. Additionally, the clinical trial is carried out in a number of phases involving different constraints applied for conducting the clinical trial. Furthermore, a clinical trial entry for every clinical trial is provided to an approving body (namely, regulatory body) to receive approval for conducting the clinical trial. Moreover, the clinical trial registered with the approving body has an entry in a list (namely, a database, a log and the like) maintained by the approving body. In addition, the clinical trial entry uniquely identifies the clinical trial associated therewith. Furthermore, the clinical trial entry can have access rights (such as a permissioned or public access rights) associated therewith. It will be appreciated that the clinical trial entry of the new treatment or known intervention can be used to access the clinical trial associated therewith. Furthermore, the at least one publication related to the clinical trial entry can be identified by analyzing and comparing a context and different parameters (namely, attributes) of the clinical trial and the at least one publication, wherein a similar context and identical or similar parameter leads to identification of a relation between the clinical trial and the at least one publication.

It will be appreciated that when a given clinical trial is ongoing, several articles, research papers and results are published documenting the findings and conclusions ascertained by the given clinical trial. However, such articles, research papers and results are not necessarily associated with the clinical trial entry of the given clinical trial. Therefore, in such a scenario, the given clinical trial may remain undocumented. Moreover, a documented clinical trial has an identified relation with publications having subject matter related thereto. In other words, the documented clinical trial has identified relation with at least one publication that provides a brief or elaborate description of use, after effects, side effects and other information related to the new treatment or intervention mentioned in the clinical trial. Beneficially, the documented clinical trial can be used for extending research on the new treatment or intervention mentioned in the clinical trial. Notably, two or more documented clinical trials can optionally have a relation therebetween. The relation between the clinical trials and the at least one publication can be used by a user for achieving information associated with the new treatment or known intervention before extending a research thereon or application of the new treatment or known intervention for treating humans. In addition, identification of related clinical trials and at least one publication related thereto in order to form the documented clinical trials prevent scientists and researchers from reworking on work (such as tests, observations and so forth) already performed an existing clinical trial and thereby saving time, effort and money.

Furthermore, the at least one publication relates to a document that includes information associated with one or more clinical trials. The at least one publication is a research paper, a conference paper, a journal, an article, a blog and the like. In addition, the at least one publication includes information associated with one or more clinical trials presented in form of text, images, graphs, audio, video, graphical image format and the like. Moreover, the at least one publication can be stored in a word format, a portable document format (PDF), a PowerPoint presentation, a webpage or any other format suitable for storing the at least one publication. Moreover, the at least one publication has an author associated therewith.

As mentioned previously, the system when operated identifies at least one publication related to the clinical trial entry to obtain the documented clinical trial. The system comprises the information repository comprising the plurality of publications. The information repository relates to a digital database that allows for retrieval of the plurality of publications by the system. The information repository can store the plurality of publications in format such as, but not limited to, Portable Document Format (PDF), Joint Photographic Experts Group (JPEG) format, Microsoft Word document format, Microsoft Excel worksheet format, Hyper Text Markup Language (HTML) format and so forth. The information repository is created by accessing various online and offline sources and collecting the plurality of publications available with the various sources. Notably, the plurality of publications includes publications from a plurality of research areas such as finance, marketing, life science, bio-medical, cloud computing and so forth. Beneficially, the information repository reduces an amount of resources (for example time, effort and money) spent on retrieval of the plurality of publications from various online and offline sources.

Furthermore, the system comprises the clinical trials registry database comprising the plurality of clinical trial entries. The clinical trials registry database may be obtained by curating databases of clinical trial entries maintained by approving bodies over a plurality of geographical location. Furthermore, the clinical trials registry database is a digital database comprising clinical trials entries associated with the plurality of clinical trials. Moreover, the clinical trials registry database may include databases of clinical trials entries, maintained by independent organizations.

Furthermore, the system comprises the server arrangement. Notably, the server arrangement is a hardware, software, firmware or a combination thereof. In addition, the server arrangement may have a centralized or distributed architecture. Furthermore, the server arrangement optionally includes one or more processors configured to access the clinical trials registry database and the information repository. Moreover, the server arrangement includes programmable and/or non-programmable components configured to store, process and/or share information stored in the clinical trials database and the information repository. Optionally, the server arrangement includes any arrangement of physical or virtual computational entities capable of enhancing information to perform various computational tasks. Furthermore, it should be appreciated that the server arrangement can be a single hardware server and/or plurality of hardware servers operating in a parallel or sequential manner. In an example, the server arrangement may include components such as memory, a processor, a network adapter and the like, to store, process and/or share information with other computing components, such as user device/user equipment. Optionally, the server arrangement is implemented as a computer program that provides various services (such as database service) to other devices, modules or apparatus.

Furthermore, the server arrangement is communicably coupled to the information repository and the clinical trials registry database. Notably, the communicable coupling of the server arrangement with the clinical trials registry database and the information repository allows the server arrangement for retrieval of clinical trial entries and the plurality of publications respectively. Furthermore, the communicable coupling can have dedicated resources for communication between the server arrangement and the clinical trials registry database and the information repository. Alternatively, the communicable coupling can be infrastructure less, wherein resources for communication are allotted whenever there is any information that is to be communicated.

Optionally, the server arrangement is communicably coupled to the clinical trials registry database and the information registry via a communication module. The communication module is an arrangement of interconnected programmable and/or non-programmable components that are configured to facilitate data communication between one or more electronic devices and/or databases. Furthermore, the communication module can include, but is not limited to, one or more peer-to-peer network, a hybrid peer-to-peer network, local area networks (LANs), radio access networks (RANs), metropolitan area networks (MANS), wide area networks (WANs), all or a portion of a public network such as the global computer network known as the Internet, a private network, a cellular network and any other communication system or systems at one or more locations. Additionally, the communication module includes wired or wireless communication that can be carried out via any number of known protocols, including, but not limited to, Internet Protocol (IP), Wireless Access Protocol (WAP), Frame Relay, or Asynchronous Transfer Mode (ATM). Moreover, any other suitable protocols using voice, video, data, or combinations thereof, can also be employed for facilitating communication of the server arrangement with the clinical trials registry database and the information repository.

Furthermore, the server arrangement is configured to obtain the plurality of publications from the information repository. Notably, the server arrangement obtains the plurality of publications by accessing the information registry in a sequential or random manner. It is to be understood, the plurality of publications obtained by the server arrangement belongs to a general research field that is not limited to Life Science, Medical Science, and the like. In other words, the plurality of publications obtained by the server arrangement from the information repository belongs to general research areas such as finance, marketing, biomedical and the like.

It will be appreciated that the plurality of publications obtained by the server arrangement from the information repository include publications from various research fields that is not limited to a research field associated with the clinical trials.

Optionally, the plurality of publications are obtained by the server arrangement based on an index number associated therewith, wherein the index number uniquely identifies a position of each of the plurality of publications within the information repository.

More optionally, the plurality of publications are obtained by the server arrangement based on an offset associated therewith, wherein the offset for a given publication when processed, identifies a memory location where the given publication is stored within the information repository.

Furthermore, optionally, the plurality of publications are obtained by the server arrangement based on a memory location associated with each of the publications in the plurality of publications.

Optionally, the plurality of publications obtained by the server are stored in a temporary memory location within the server arrangement for further processing thereof.

Moreover, the server arrangement is configured to analyze the plurality of publications, using the filtering module, to determine the filtered set of publications, wherein each of the publications in the filtered set is related to clinical trial research. The filtering module is operable to perform a contextual analysis of each of the publications in the plurality of publications, wherein the plurality of publications includes publications from the plurality of research areas. The filtering module is accountable for separating publications relating to clinical trial research from publications relating to other fields. Notably, the separated publications relating to clinical trial research forms the filtered set of publications.

Furthermore, the filtering module is enabled to identify an occurrence of specific keywords and/or synonyms thereof in the plurality of publications and context associated with the identified keywords. Consequently, the filtering module determines the filtered set of publications based on occurrence and context of the identified keywords and/or synonyms thereof.

In an example, the plurality of publications may include publications having subject matter associated with wireless sensor networks, treatment of Tuberculosis, energy conservation, hair fall treatment, effects of global warming. The server arrangement analyzes the publications using the filtering module, wherein the filtering module obtains a filtered set of publications including publications having subject matter associated with treatment of Tuberculosis and hair fall treatment.

Optionally, the filtering module performs the contextual analysis by way of a parsing module, wherein the parser is configured to perform parsing on each of the publications within the plurality of publications. Notably, parsing a content of each of the publications within the plurality of publications allows for an efficient and complete analysis of the plurality of publications.

In an embodiment, the filtering module employs machine learning algorithms. The filtering module employs machine learning algorithms for training thereof in order to identify publications relating to clinical trial research from the plurality of publications. In addition, the machine learning algorithms allow the filtering module to be trained for identifying newly discovered keywords relating to the clinical trial research. Notably, the machine learning algorithms employ artificial intelligence that provide the filtering module an ability to automatically learn and improve from experience.

In an embodiment, the filtering module, employing machine learning algorithms, is trained using supervised learning techniques. The filtering module is trained using one or more sets of labelled data. In addition, the supervised learning technique trains the filtering module by way of providing an input of a plurality of publications and a desired output of a filtered set. Therefore, the filtering module can adjust a functioning thereof for achieving the desired output.

In an embodiment, a labelled training dataset for the filtering module comprises labelled publications relating to clinical trial research as a positive training dataset and labelled publications unrelated to clinical trial research as a negative training dataset. Specifically, the labelled training data is provided to the filtering module as an input for training of the filtering module to identify publication related to clinical trial research. The training of filtering module enables the filtering module to identify publications related to clinical trial research and publication unrelated to clinical trial research. Specifically, the filtering module, employing machine learning algorithms, identifies characteristics of publications related and unrelated to clinical trial research from the labelled training dataset. Consequently, the filtering module is trained to filter publications related to clinical trial research from the plurality of publications.

Optionally, the positive training dataset includes keywords, sentences, phrases and/or publications relating to the publications related to the clinical trial research. Furthermore, the negative dataset includes keywords, sentences, phrases and/or publications unrelated to the clinical trial research. In other words, the negative dataset includes keywords, sentences, phrases and/or publications related to the plurality of research areas excluding the clinical trial research.

Optionally, the server arrangement is operable to create the labelled training dataset for training the filtering module.

Optionally, the filtering module is trained using unsupervised learning techniques or recurrent learning technique.

Moreover, the server arrangement is configured to obtain the plurality of clinical trial entries from the clinical trials registry database. The plurality of clinical trial entries are obtained from one or more approving body. The server arrangement accesses the clinical trials registry in a sequential or random order for retrieving the plurality of clinical trial entries. The plurality of clinical trial entries obtained from the clinical trials registry database are retrieved in form of a list, a table or any other form of representing data.

Optionally, the plurality of clinical trial entries obtained by the server arrangement are stored in a temporary memory location within the server arrangement.

The server arrangement is configured to analyze the context of each of the publications in the filtered set and each of the plurality of clinical trial entries using the mapping module to identify the relationship of each of the publication with at least one of the plurality of clinical trial entries. The mapping module analyzes the context of each of the publications in the filtered set and each of the clinical trials related with the plurality of clinical trial entries. Notably, the mapping module performs the contextual analysis of each of the publications in the filtered set and clinical trials related with each of the plurality of clinical trial entries on sentence level, paragraph level and on document level. In addition, the mapping module allows for identification of synonyms of words used in each of the publications in the filtered set and clinical trials related with each of the plurality of clinical trial entries. Consequently, the mapping module enables determination of a different context using similar words as well as determination of similar context using different words. Furthermore, such contextual analysis of each of the publications in the filtered set and clinical trials related with each of the plurality of clinical trial entries allows for comparison of contexts of each of the publications in the filtered set with contexts of each of the plurality of clinical trial entries, in order to identify the relationship between the publications in the filtered set and the plurality of clinical trial entries. Moreover, the relationship of each of the publication with at least one of the plurality of clinical trial entries is based upon a subject matter discussed (namely, mentioned, elaborated, reviewed and the like) in each of the publications.

It will be appreciated that for a given publication, relationship with a clinical trial entry may not be identified. In other words, the given publication may not be mapped with any clinical trial entry of the plurality of clinical trial entries. It is to be understood, in such an instance, that the clinical trial entry related to the given publication may not be stored in the clinical trials registry database. Similarly, for a given clinical trial entry, relationship with a publication may not be identified. In other words, the given clinical trial entry may not be mapped with any publication in the filtered set of publications (or, the plurality of publications). It is to be understood, in such an instance, that any publication related to the given clinical trial entry may not be stored in the information repository.

In an embodiment, the mapping module employs machine learning algorithms. The mapping module employs machine learning algorithms for training thereof in order to identify relationship of each of the publication with at least one of the plurality of clinical trial entries. In addition, the machine learning algorithms allow the mapping module to be trained for identifying characteristics of each of the publications and each of the plurality of clinical trials. Notably, the machine learning algorithms employ artificial intelligence that provides the mapping module an ability to automatically learn and improve from experience.

In an embodiment, the mapping module, employing machine learning algorithms, are trained using supervised learning techniques. Specifically, the mapping module is provided with a labelled training dataset for training thereof. The labelled training data is developed in a manner such that the mapping module can assimilate contextual relationships between a clinical trial entry and a publication. Notably, the mapping module is configured to learn from the training data characteristics of related clinical trial entries and publications.

In an embodiment, a labelled training dataset for the mapping module comprises labelled clinical trial entries and labelled related publications as a positive training dataset, and labelled clinical trial entries and labelled unrelated publications as a negative training dataset. The mapping module is trained for identifying relationship of each of the publications with at least one of the plurality of clinical trial entries as well as for separating publications from clinical trial entries not having a relationship therewith. Notably, the mapping module is trained for identifying relationship of each of the publications with at least one of the plurality of clinical trial entries using the positive dataset. Furthermore, the positive dataset includes identified relationships of publications with at least one clinical trial entry. The negative dataset includes publications and at least one clinical trial having no relationship therebetween.

Optionally, the mapping module is trained using unsupervised learning techniques or recurrent learning technique.

Furthermore, the server arrangement is configured to associate the plurality of clinical trial entries with publications related thereto to obtain the documented clinical trials. Notably, the server arrangement establishes a direct or indirect link between the plurality of clinical trial entries and publications related thereto. In an instance, when the server arrangement establishes the direct link, the plurality of clinical trials and the publications related thereto are stored together. In another instance, when the server arrangement establishes the indirect link, the plurality of clinical trials and the publications related thereto are linked by way of pointers. It is to be understood that storing the plurality of clinical trials and the publications related thereto together or linking the plurality of clinical trials and the publications related thereto by way of pointers are explained herein merely for sake of understanding and should not be used for limiting the scope of invention. Beneficially, associating the plurality of clinical trial entries with publications related thereto allows for quick and effecting retrieval of authentic and updated information regarding the plurality of clinical trial entries.

In an embodiment, the server arrangement is further configured to determine, using a classification module, whether the at least one publication related to a given clinical trial entry is a primary publication or a secondary publication for the given clinical trial. Typically, for a clinical trial entry, there are multiple publications associated therewith. In such multiple publications associated with the clinical trial entry, the publications, comprising information related exclusively with the clinical trial entry, are primary publications. Furthermore, publications, comprising information that is not exclusively related to the clinical trial entry, are secondary publications. In other words, information in a secondary publication may relate peripherally to the clinical trial entry or may comprise information related to multiple clinical trial entries. Additionally, a secondary publication may refer to a research paper including insights derived from the results of the clinical trial entry. Furthermore, the classification module analyses the relationships between the plurality of clinical trial entries and the publications related thereto in order to determine if a given publication is related to more than one clinical trial entry from the plurality of clinical trial entries. Furthermore, the primary publication for the given clinical trial is published prior to a publication of the secondary publication for the given clinical trial. In addition, the secondary publication for the given clinical trial may include a reference to the primary publication of the given clinical trial. Moreover, the secondary publications may be used to support content of the primary publications. Optionally, an investigator of the clinical trial may be an author of a primary publication of a given clinical trial.

In an embodiment, the classification module employs machine learning algorithms, trained using supervised learning techniques. The classification module employs machine learning algorithms for training thereof in order to analyze relationship of each of the publication with associated clinical trial entries. Notably, the machine learning algorithms employ artificial intelligence that provides the classification module an ability to automatically learn and improve. Furthermore, the classification module is trained using one or more set of labelled training dataset.

In an embodiment, a labelled training dataset for the classification module comprises labelled clinical trial entries and associated related primary and secondary publications. The classification module is trained using supervised learning techniques by way of the labelled training dataset. Specifically, the classification module is configured to analyze the labelled clinical trial entries and associated related primary and secondary publications to distinguish between a context of the associated related primary publications and a context of the associated related secondary publications with respect to a labelled clinical trial entry. Notably, since the context of associated related primary publications may be substantially distinguishable from the context of the associated related secondary publications, the classification module identifies such differences to be trained in the classification.

Optionally, the classification module is trained using unsupervised learning techniques or recurrent learning technique.

The present disclosure also relates to the method as described above. Various embodiments and variants disclosed above apply mutatis mutandis to the method.

Optionally, the method further comprises determining, using a classification module, whether the at least one publication related to a given clinical trial entry is a primary publication or a secondary publication for the given clinical trial.

Optionally, in the method, the filtering module and the mapping module employ machine learning algorithms.

Optionally, the method further comprises training the filtering module and the mapping module, employing machine learning algorithms, using supervised learning techniques.

Optionally, in the method, a labelled training dataset for the filtering module comprises labelled publications relating to clinical trial researches as a positive training dataset and labelled publications unrelated to clinical trial research as a negative training dataset.

Optionally, in the method, a labelled training dataset for the mapping module comprises clinical trial entries and associated related publications as a positive training dataset, and clinical trial entries and unrelated publications as a negative training dataset.

Optionally, the method further comprises training the classification module employs machine learning algorithms, using supervised learning.

Optionally, in the method, a labelled training dataset for the classification module comprises clinical trial entries and associated related primary and secondary publications.

DETAILED DESCRIPTION OF THE DRAWINGS

Figure 1:
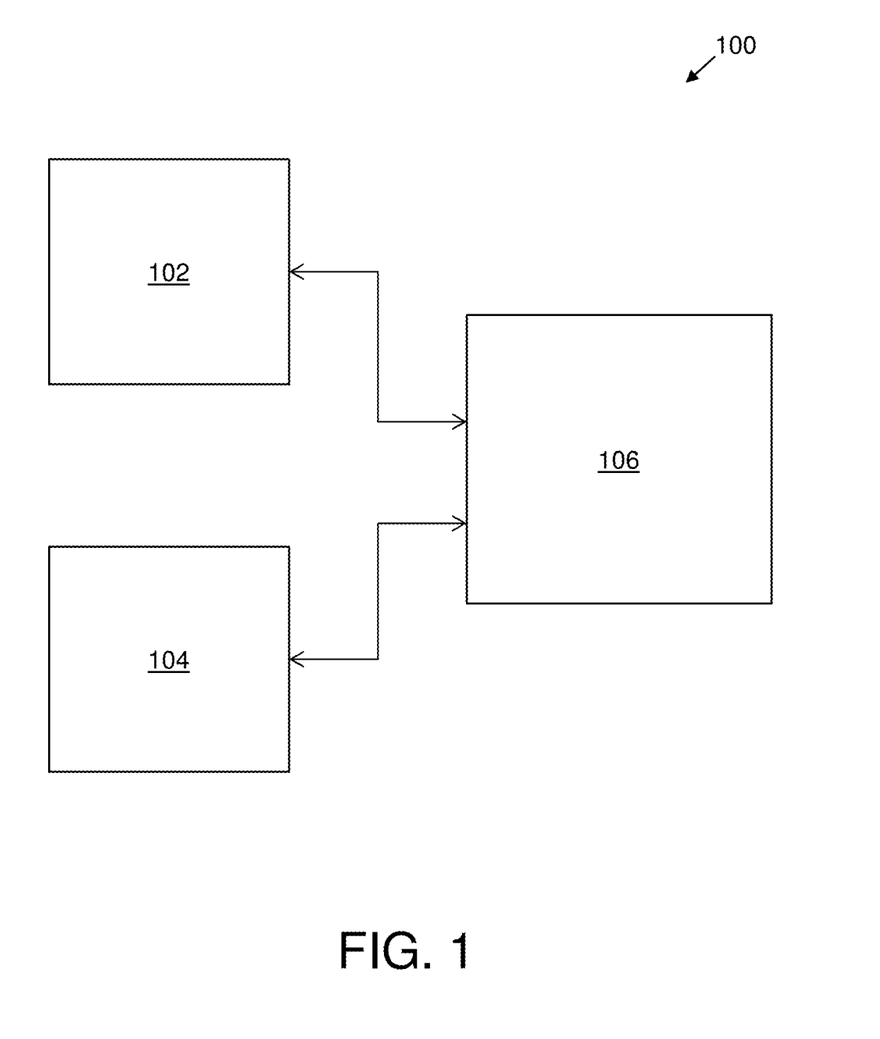
FIG. 1 is a block diagram of a system for documenting clinical trials, in accordance with an embodiment of the present disclosure.

Referring to FIG. 1, illustrated is a block diagram of a system 100 for documenting clinical trials, in accordance with an embodiment of the present disclosure. The system when operated identifies at least one publication related to a clinical trial entry to obtain a documented clinical trial. Furthermore, the system 100 comprises an information repository 102 comprising a plurality of publications, a clinical trials registry database 104 comprising a plurality of clinical trial entries and a server arrangement 106. The server arrangement 106 is communicably coupled to the information repository 102 and the clinical trials registry database 104. Notably, the server arrangement 106 is configured to obtain the plurality of publications from the information repository 102. In addition, the server arrangement 106 is configured to obtain the plurality of clinical trial entries from the clinical trials registry database 104.

Figure 2:
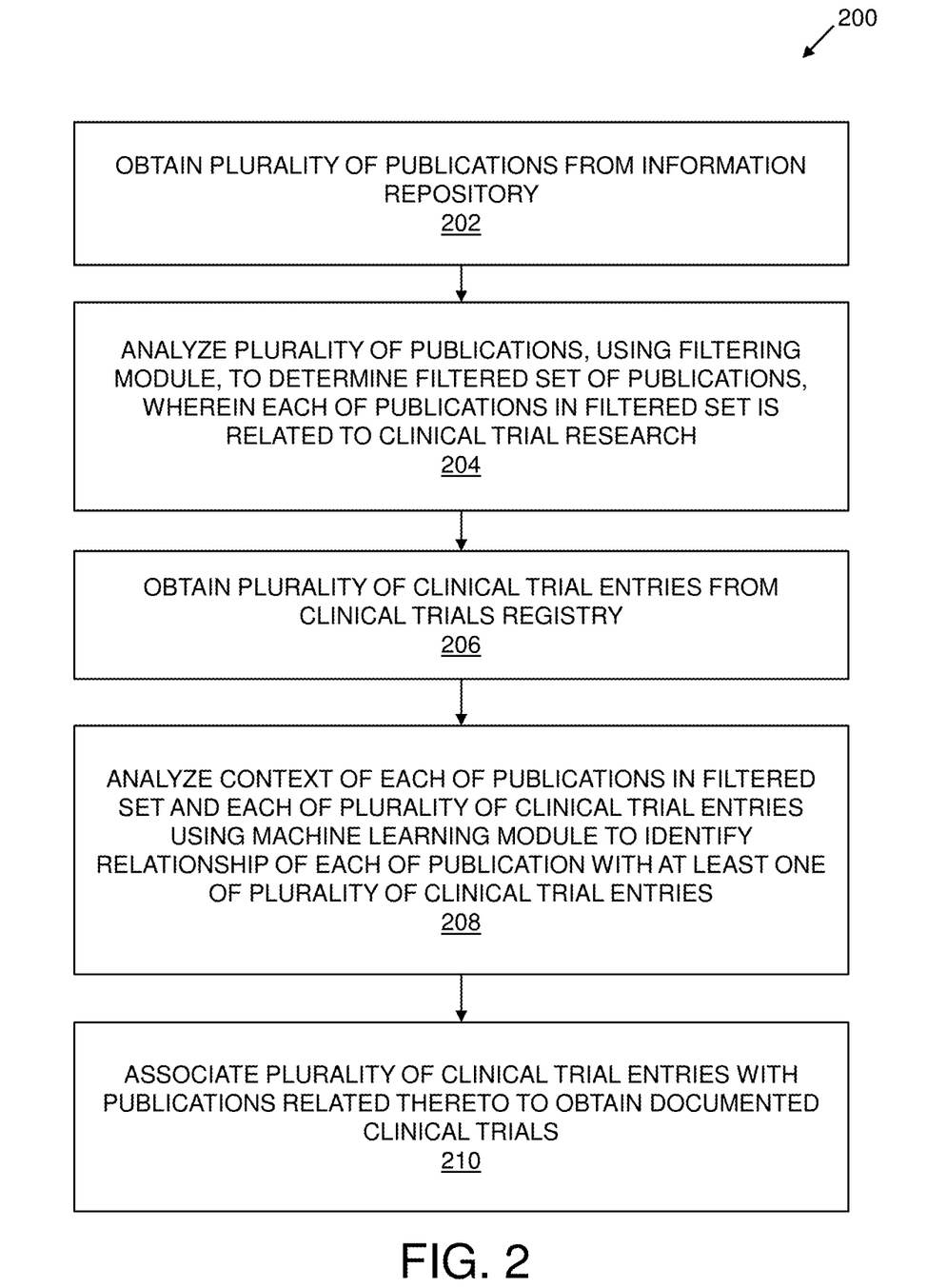
FIG. 2 is a flow chart depicting steps of a method for documenting clinical trials, in accordance with an embodiment of the present disclosure.

Referring to FIG. 2, illustrated is a flow chart depicting steps of a method 200 for documenting clinical trials, in accordance with an embodiment of the present disclosure. At step 202, a plurality of publications are obtained from an information repository. At step 204, the plurality of publications are analyzed using a filtering module, to determine a filtered set of publications. Notably, each of the publications in the filtered set is related to clinical trial research. At step 206, a plurality of clinical trial entries are obtained from a clinical trials registry. Consequently, at step 208, a context of each of the publications in the filtered set and each of the plurality of clinical trial entries is analyzed using a machine learning module to identify a relationship of each of the publication with at least one of the plurality of clinical trial entries. At step 210, the plurality of clinical trial entries are associated with publications related thereto to obtain documented clinical trials.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

What is claimed is:

1. A system for documenting clinical trials, the system when operated identifies one or more publications related to a clinical trial entry to obtain a documented clinical trial, wherein the system comprises:
    an information repository comprising a plurality of publications;
    a clinical trials registry database comprising a plurality of clinical trial entries; and
    a server arrangement communicably coupled to the information repository and the clinical trials registry database, wherein the server arrangement is configured to:
    train machine learning algorithms using supervised learning using a labelled training dataset;
    obtain the plurality of publications from the information repository;
    analyze the plurality of publications to determine a filtered set of publications, wherein each of the publications in the filtered set is related to clinical trial research;
    obtain the plurality of clinical trial entries from the clinical trials registry database;
    analyze a context of each of the publications in the filtered set and each of the plurality of clinical trial entries using the trained machine learning algorithms to identify a relationship of each of the publications in the filtered set with at least one of the plurality of clinical trial entries;
    identify associations between each of the publications in the filtered set and the at least one of the plurality of clinical trial entries based on the identified relationship, to obtain documented clinical trials, wherein identifying associations refers to establishing direct and indirect relationships between each of the publications in the filtered set and the at least one of the plurality of clinical trial entries;
    determine, whether a given publication of the one or more publications related to the clinical trial entry is a primary publication or a secondary publication for the documented clinical trial based on the identified associations, wherein the primary publication comprises information that is exclusively related to the clinical trial entry and the secondary publication comprises information that is not exclusively related to the clinical trial entry; and
    sort the one or more publications related to the clinical trial entry based on the determination of whether the given publication is a primary publication or a secondary publications.

2. The system of claim 1, wherein the labelled training dataset for the server arrangement comprises labelled publications relating to clinical trial research as a positive training dataset and labelled publications unrelated to clinical trial research as a negative training dataset.

3. The system of claim 1, wherein the labelled training dataset employed by the server arrangement comprises labelled clinical trial entries and labelled related publications as a positive training dataset, and labelled clinical trial entries and labelled unrelated publications as a negative training dataset.

4. The system of claim 1, wherein the labelled training dataset for the server arrangement comprises labelled clinical trial entries, and associated related primary and secondary publications.

5. A method of documenting clinical trials, the method comprises identifying one or more publications related to a clinical trial entry to obtain a documented clinical trial, wherein the method is implemented via a system comprising a server arrangement coupled to an information repository and a clinical trials registry database, wherein the method comprises:
    training machine learning algorithms using supervised learning using a labelled trainings dataset;
    obtaining a plurality of publications from the information repository;
    analyzing the plurality of publications to determine a filtered set of publications, wherein each of the publications in the filtered set is related to clinical trial research;
    obtaining a plurality of clinical trial entries from a clinical trials registry database;
    analyzing a context of each of the publications in the filtered set and each of the plurality of clinical trial entries using the trained machine learning algorithms to identify a relationship of each of the publication in the filtered set with at least one of the plurality of clinical trial entries;
    identifying associations between each of the publications in the filtered set and the at least one of the plurality of clinical trial entries to obtain documented clinical trials, wherein identifying associations refer to establishing direct and indirect relationship between each of the publications in the filtered set and the at least one of the plurality of clinical trial entries;
    determining, whether a given publication of the one or more publications related to the clinical trial entry is a primary publication or a secondary publication for the documented clinical trial based on the identified associations,
    wherein the primary publication comprise information that is exclusively related to the clinical trial entry and secondary publication comprise information that is not exclusively related to the clinical trial entry; and
    sorting the one or more publications related to the clinical trial entry based on the determination of whether the given publication is a primary publication or a secondary publication.

6. The method of claim 5, wherein labelled training dataset for the server arrangement comprises labelled publications relating to clinical trial researches as a positive training dataset and labelled publications unrelated to clinical trial research as a negative training dataset.

7. The method of claim 5, wherein labelled training dataset for the server arrangement comprises labelled clinical trial entries and labelled related publications as a positive training dataset, and labelled clinical trial entries and labelled unrelated publications as a negative training dataset.

8. The method of claim 5, wherein the labelled training dataset for the server arrangement comprises labelled clinical trial entries, and associated related primary and secondary publications.

* * * * *